United States Patent [19]

Schnettler et al.

[11] 4,405,635

[45] Sep. 20, 1983

[54] 4-AROYLIMIDAZOL-2-ONES AND THEIR USE AS PHARMACEUTICALS

[75] Inventors: Richard A. Schnettler; Richard C. Dage, both of Cincinnati, Ohio; Johann M. Grisar, Strasbourg, France

[73] Assignee: Merrell Dow Pharmaceuticals Inc., Cincinnati, Ohio

[21] Appl. No.: 417,805

[22] Filed: Sep. 13, 1982

Related U.S. Application Data

[63] Continuation-in-part of Ser. No. 373,457, Apr. 30, 1982, abandoned, which is a continuation of Ser. No. 235,453, Feb. 18, 1981, abandoned, which is a continuation-in-part of Ser. No. 159,048, Jun. 13, 1980, abandoned, which is a continuation-in-part of Ser. No. 119,207, Feb. 7, 1980, abandoned, which is a continuation-in-part of Ser. No. 49,808, Jun. 18, 1979, abandoned.

[51] Int. Cl.³ .................. A61K 31/415; C07D 233/70
[52] U.S. Cl. ........................ 424/273 R; 424/248.54; 424/250; 424/267; 544/139; 544/370; 546/210; 548/317; 548/318; 548/321
[58] Field of Search .................. 548/321, 318, 317; 544/139, 370; 546/210; 424/248.54, 250, 267, 273 R

[56] References Cited

U.S. PATENT DOCUMENTS 2,441,933  5/1948  Duschinsky .................. 548/321
2,514,380  7/1950  Duschinsky .................. 548/321

OTHER PUBLICATIONS

Duschinsky and Dolan "J. Am. Chem. Soc." vol. 68, pp. 2350-2355 (1946); ibid. vol. 70, pp. 657-662 (1948); ibid. vol. 67 pp. 2079-2084 (1945).
Rozin et al. "Khim. Geterotsikl. Soedin." vol. 4, No. 4, pp. 698-701 (1968).
Dage et al. "Fed. Proc." vol. 39, p. 1105 (1980).
Hsieh et al. "Fed. Proc." vol. 39, p. 1106 (1980).

Primary Examiner—Robert T. Bond
Attorney, Agent, or Firm—Stephen L. Nesbitt; Raymond A. McDonald; Gary D. Street

[57] ABSTRACT

Novel 4-aroylimidazol-2-ones of the following general structure which are useful as antihypertensives, cardiotonics, antithrombotics, bronchodilators and uterospasmolytics

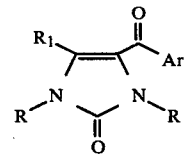

wherein Ar is 2-furyl, 2-thienyl or phenyl, the latter of which may optionally be substituted with one or two X groups; X is halogen, hydroxy, $C_{1-4}$ alkyl, $C_{1-4}$ alkoxy, methylenedioxy, $C_{1-4}$ alkylthio, $C_{1-4}$ alkylsulfoxide, $C_{1-4}$ alkylsulfone, $CF_3$, $-SO_2N(R_2)_2$, $NR_3R_4$, pyrrolidino, piperidino, morpholino, piperazino or N'-alkylpiperazino, R is hydrogen, $C_{1-4}$ alkyl, $C_{1-4}$ alkylcarbonyl or benzyl; each of $R_1$, $R_2$, $R_3$ and $R_4$ are hydrogen or $C_{1-4}$ alkyl; and the pharmaceutically acceptable salts thereof.

16 Claims, No Drawings

4-AROYLIMIDAZOL-2-ONES AND THEIR USE AS PHARMACEUTICALS

This is a continuation-in-part of copending U.S. application Ser. No. 373,457, filed Apr. 30, 1982 abandoned, which is a continuation of U.S. Ser. No. 235,453, filed Feb. 18, 1981, now abandoned, which is a continuation-in-part of U.S. Ser. No. 159,048, filed June 13, 1980, now abandoned, which is a continuation-in-part of U.S. Ser. No. 119,207, filed Feb. 7, 1980, now abandoned, which is a continuation-in-part of U.S. Ser. No. 49,808, filed June 18, 1979, now abandoned.

FIELD OF THE INVENTION

This invention relates to 4-aroylimidazol-2-ones; their use as antihypertensive, cardiotonics, antithrombotics, bronchodilators and uterospasmolytics; their pharmaceutical compositions; and their preparation.

DESCRIPTION OF THE PRIOR ART

The closest prior art known to the applicants is found in U.S. Pat. Nos. 2,514,380 and 2,441,933, as well as in R. Duschinsky and L. A. Dolan, *J. Am. Chem. Soc.* 68, 2350–55 (1946); ibid. 70, 657–62 (1948); ibid. 67, 2079–84 (1945); and Y. A. Rozin, E. P. Dorienko and Z. V. Pushkareva, *Khim. Geterotsikl. Soedin.*, 4(4), 698–701 (1968). These references disclose the preparation of chemical intermediate utility of the following compounds:
4-benzoyl-1,3-dihydro-2H-imidazol-2-one;
4-benzoyl-1,3-diacetyl-1,3-dihydro-2H-imidazol-2-one;
4-benzoyl-1,3-dihydro-5-(lower alkyl)-2H-imidazol-2-one;
4-benzoyl-1,3-diacetyl-1,3-dihydro-5-methyl-2H-imidazol-2-one;
1,3-diacetyl-1,3-dihydro-4-(3,4-dimethylbenzoyl)-2H-imidazol-2-one;
1,3-dihydro-4-(hydroxybenzoyl)-2H-imidazol-2-one;
1,3-dihydro-4-(hydroxybenzoyl)-5-(lower alkyl)-2H-imidazol-2-one;
1,3-dihydro-4-(3,4-dihydroxybenzoyl)-2H-imidazol-2-one;
1,3-dihydro-4-(4-nitrobenzoyl)-2H-imidazol-2-one;
1,3-dihydro-4-methyl-5-(4-nitrobenzoyl)-2H-imidazol-2-one,
4-(3-aminobenzoyl)-1,3-dihydro-2H-imidazol-2-one,
4-(4-aminobenzoyl)-1,3-dihydro-2H-imidazol-2-one, and
4-(4-aminobenzoyl)-1,3-dihydro-5-methyl-2H-imidazol-2-one,
however, no pharmaceutical utility for the 4-aroylimidazol-2-ones of the present invention has been previously taught.

SUMMARY OF THE INVENTION

This invention is directed to pharmaceutically active 4-aroylimidazol-2-ones of general Formula 1

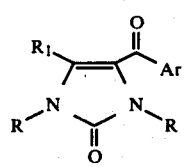

Formula 1 wherein Ar is 2-furyl, 2-thienyl, phenyl, phenyl monosubstituted at the ortho, meta or para position with $X_1$, or disubstituted phenyl substituted at the para position with $X_2$ and at the ortho or meta position with $X_3$; $X_1$ is halogen, hydroxy, a straight or branched chain lower alkyl of from 1 to 4 carbon atoms, a straight or branched chain lower alkoxy of from 1 to 4 carbon atoms, a straight or branched chain lower alkylthio of from 1 to 4 carbon atoms, trifluoromethyl, a straight or branched chain lower alkylsulfoxide of from 1 to 4 carbon atoms, a straight or branched chain lower alkylsulfone of from 1 to 4 carbon atoms, $-SO_2N(R_2)_2$, $NR_3R_4$, pyrrolidino, piperidino, morpholino, piperazino or N'-alkylpiperazino; $X_2$ and $X_3$ are halogen, hydroxy, a straight or branched chain lower alkyl of from 1 to 4 carbon atoms, a straight or branched chain lower alkoxy of from 1 to 4 carbon atoms or when $X_3$ is at the meta position, $X_2$ and $X_3$ taken together may be a methylenedioxy optionally substituted by one or two methyl groups; R is hydrogen, a straight or branched chain lower alkyl of from 1 to 4 carbon atoms, a straight or branched chain lower alkylcarbonyl of from 1 to 4 carbon atoms, or a benzoyl group; each of $R_1$, $R_2$, $R_3$ and $R_4$ is hydrogen or a straight or branched chain lower alkyl of from 1 to 4 carbon atoms; or a pharmaceutically acceptable salt thereof. These compounds are useful as antihypertensives, cardiotonics, antithrombotics, bronchodilators and uterospasmolytics. This invention is directed, furthermore, to the process of preparing the 4-aroylimidazol-2-ones as well as their pharmaceutical compositions.

DESCRIPTION OF THE PREFERRED EMBODIMENTS

Illustrative examples of a straight or branched chain lower alkyl of from 1 to 4 carbon atoms as used herein are methyl, ethyl, n-propyl, isopropyl, n-butyl and isobutyl.

Illustrative examples of a straight or branched chain lower alkoxy of from 1 to 4 carbon atoms as used herein are methoxy, ethoxy, n-propoxy, isopropoxy, n-butoxy and isobutoxy.

As used herein, the term halogen is taken to mean fluorine, chlorine, bromine or iodine.

As used herein, the term halide is taken to mean fluoride, chloride, bromide, or iodide.

As used herein, the term a straight or branched chain lower alkylthio of from 1 to 4 carbon atoms is taken to mean a group of the structure, S-alkyl, wherein the alkyl moiety is a straight or branched chain alkyl of from 1 to 4 carbon atoms and may be, for example, methyl, ethyl, n-propyl, isopropyl, n-butyl or isobutyl.

As used herein, the term a straight or branched chain lower alkylsulfoxide of from 1 to 4 carbon atoms is taken to mean a group of the structure, S(O)alkyl, wherein the alkyl moiety is a straight or branched chain alkyl of from 1 to 4 carbon atoms and may be, for example, methyl, ethyl, n-propyl, isopropyl, n-butyl or isobutyl.

As used herein, the term a straight or branched chain lower alkylsulfone of from 1 to 4 carbon atoms is taken to mean a group of the structure, $S(O)_2$alkyl, wherein the alkyl moiety is a straight or branched chain alkyl of from 1 to 4 carbon atoms and may be, for example, methyl, ethyl, n-propyl, isopropyl, n-butyl or isobutyl.

As used herein, the term methylenedioxy optionally substituted by one or two methyl groups is taken to mean methylenedioxy, ethylenedioxy or isopropylidenedioxy.

As used herein, the term a benzoyl group is taken to mean a group of the formula —(CO)C$_6$H$_5$.

As used herein, the term a straight or branched chain lower alkylcarbonyl of from 1 to 4 carbon atoms is taken to mean a group of the structure

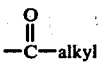

wherein the alkyl moiety is a straight or branched chain lower alkyl of from 1 to 4 carbon atoms and may be, for example, methyl, ethyl, n-propyl, isopropyl, n-butyl or isobutyl.

As used herein, the term N'-alkyl-piperazino is taken to mean a group of the structure

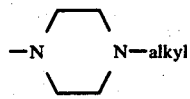

wherein the alkyl moiety is a straight or branched chain lower alkyl of from 1 to 4 carbon atoms and may be, for example, methyl, ethyl, n-propyl, isopropyl, n-butyl or isobutyl.

The preferred compounds of this invention are those compounds of Formula 1 wherein R is hydrogen and X$_1$ is piperidino, pyrrolidino, morpholino, piperazino, N'-alkylpiperazino, a straight or branched chain lower alkylthio of from 1 to 4 carbon atoms, a straight or branched chain lower alkylsulfoxide of from 1 to 4 carbon atoms, or a straight or branched chain lower alkylsulfone of from 1 to 4 carbon atoms. Other preferred compounds of this invention are those compounds of Formula 1 wherein Ar is an unsubstituted phenyl and where X$_2$ and X$_3$ are a straight or branched chain lower alkoxy of from 1 to 4 carbon atoms.

The more preferred compounds of this invention are those compounds of Formula 1 wherein R$_1$ is hydrogen, methyl or ethyl and X$_1$ is at the para position and is pyrrolidino, morpholino, piperazino, N'-alkyl-piperazino, a straight or branched chain lower alkylthio of from 1 to 4 carbon atoms, a straight or branched chain lower alkylsulfoxide of from 1 to 4 carbon atoms or a straight or branched chain lower alkylsulfone of from 1 to 4 carbon atoms. Other more preferred compounds of this invention are those compounds of Formula 1 wherein R$_1$ is hydrogen, methyl or ethyl and X$_3$ is at the meta position and where X$_2$ and X$_3$ are a straight or branched chain lower alkoxy of from 1 to 4 carbon atoms or together are a methylenedioxy optionally substituted by one or two methyl groups.

The most preferred compounds of this invention are those compounds of Formula 1 wherein R is hydrogen, R$_1$ is methyl or ethyl and X$_1$ is at the para position and is methylthio, methylsulfoxide or methylsulfone, or wherein R is hydrogen, R$_1$ is methyl or ethyl and X$_3$ is at the meta position and X$_2$ and X$_3$ are methoxy or together are a methylenedioxy.

As examples of compounds of general Formula 1 there may be mentioned the following:
4-benzoyl-1,3-dihydro-5-methyl-2H-imidazol-2-one,
1,3-dihydro-4-methyl-5-(2-thienoyl)-2H-imidazol-2-one,
1,3-dihydro-4-methyl-5-(3,4-methylenedioxybenzoyl)-2H-imidazol-2-one,
1,3-dimethyl-4-benzoyl-2H-imidazol-2-one,
1,3-dihydro-4-(4-methoxybenzoyl)-5-methyl-2H-imidazol-2-one,
4-benzoyl-1,3-diacetyl-1,3-dihydro-5-methyl-2H-imidazol-2-one;
1,3-dihydro-4-(3,4-dimethoxybenzoyl)-5-methyl-2H-imidazol-2-one,
1,3-dihydro-4-(2-furanoyl)-5-methyl-2H-imidazol-2-one,
1,3-dihydro-4-(2-thienoyl)-2H-imidazol-2-one,
4-benzoyl-1,3-dihydro-2H-imidazol-2-one,
1,3-dihydro-4-(2-furanoyl)-2H-imidazol-2-one,
1,3-dihydro-4-(4-methoxybenzoyl)-2H-imidazol-2-one,
1,3-dihydro-4-(4-fluorobenzoyl)-5-methyl-2H-imidazol-2-one,
4-(2-chlorobenzoyl)-1,3-dihydro-5-methyl-2H-imidazol-2-one,
4-(4-chlorobenzoyl)-1,3-dihydro-5-methyl-2H-imidazol-2-one,
1,3-dihydro-4-methyl-5-(4-piperidinobenzoyl)-2H-imidazol-2-one,
1,3-dihydro-4-methyl-5-(4-morpholinobenzoyl)-2H-imidazol-2-one,
1,3-dihydro-4-methyl-5-(4-pyrrolidinobenzoyl)-2H-imidazol-2-one,
1,3-dihydro-4-(4-dimethylaminobenzoyl)-5-methyl-2H-imidazol-2-one,
1,3-dihydro-4-methyl-5-[4-(4-methylpiperazinobenzoyl)]-2H-imidazol-2-one,
1,3-dihydro-4-ethyl-5-(4-methoxybenzoyl)-2H-imidazol-2-one,
1,3-dihydro-4-ethyl-5-[4-(methylthio)benzoyl]-2H-imidazol-2-one,
1,3-dihydro-4-(4-hydroxybenzoyl)-5-methyl-2H-imidazol-2-one, and
1,3-dihydro-4-methyl-5-[4-(methylthio)benzoyl]-2H-imidazol-2-one.

When R is hydrogen in Formula 1 compounds, the several tautomeric forms of general Formula 2 as possible;

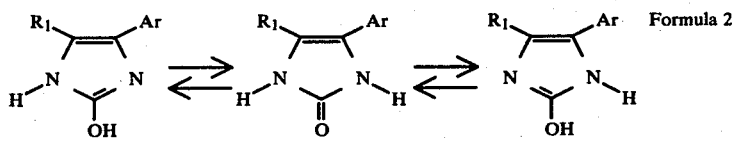

wherein R$_1$ and Ar are as defined in Formula 1. These acidic tautomers may form pharmaceutically active salts of general Formula 3

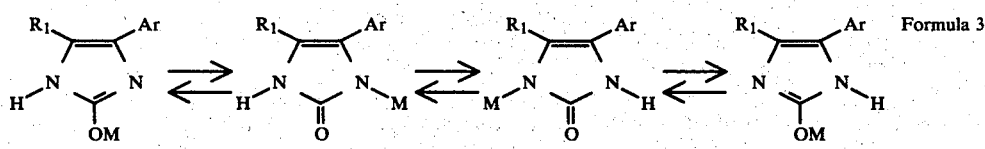

wherein $R_1$ and Ar are as defined in Formula 1, and M is a pharmaceutically acceptable alkali metal, such as sodium or potassium; alkaline earth metal, such as calcium or magnesium; transition metal, such as zinc or iron; main group metal; ammonium or organic ammonium ion, such as tetramethylammonium ion. Throughout this disclosure the term imidazol-2-one shall be taken to mean any of the tautomers of Formula 2 and a pharmaceutically acceptable salt of an imidazol-2-one shall be taken to mean any tautomer of Formula 3.

The 4-aroylimidazol-2-ones of this invention wherein R is hydrogen may be prepared by a Friedel-Crafts acylation of an imidazol-2-one of Formula 4:

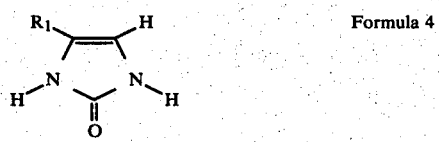

wherein $R_1$ is as defined in Formula 1. The acylating agent may be a 2-furanoyl halide, preferably 2-furanoyl chloride, a 2-thienoyl halide, preferably 2-thienoyl chloride, or a benzoyl halide, preferably a benzoyl chloride, of Formulas 5a, 5b or 5c.

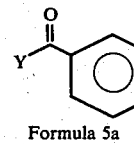 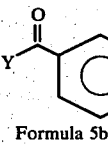 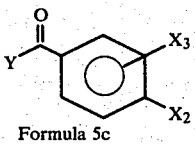

Formula 5a    Formula 5b    Formula 5c wherein Y is a halogen and $X_1$, $X_2$ and $X_3$ are as defined in Formula 1 or may additionally be any group which can be converted to the desired $X_1$, $X_2$ or $X_3$ substituent subsequent to the Friedel-Crafts reaction such as a blocking group or a nitro group which can be converted, via the diazonium ion, to a variety of other substituents by chemistry generally known in the art. Furthermore, the Friedel-Crafts reaction may be performed on the free acid or its corresponding acid anhydride instead of the aroyl halides mentioned hereinabove employing essentially identical reaction conditions. These alternate reactions are more fully described in Olah, "Friedel-Crafts and Related Reactions," Vol. III, part 1, Interscience Publications, John Wiley and Sons, New York, 1964.

The Friedel-Crafts reactions of this invention are performed by premixing about 1 molar equivalent of the appropriate imidazol-2-one with about 1 molar equivalent to about 10 molar equivalents, preferably about 2 molar equivalents, of a Lewis acid catalyst in a suitable solvent, for example, petroleum ethers; a chlorinated hydrocarbon, such as carbon tetrachloride, ethylene chloride, methylene chloride or chloroform; a chlorinated aromatic, such as 1,2,4-trichlorobenzene or o-dichlorobenzene; carbon disulfide; or preferably nitrobenzene. About 1 molar equivalent to about 10 molar equivalents, preferably about 1.1 molar equivalents of the appropriate aroyl compound is added, preferably dropwise, to the mixture of imidazol-2-one, Lewis acid, and solvent and the reaction is allowed to proceed for about ½ hour to about 100 hours, preferably from about 1 hour to about 10 hours depending on the reactants, the solvent, and the temperature which can be from about −78° to about 150° C., preferably about 0° to about 100° C., most preferably about 60° C. The resulting aroylimidazol-2-one may be isolated from the reaction mixture by any suitable art-known procedure, preferably by quenching the reaction mixture with ice water and subsequently removing the product by filtration or extraction and solvent removal.

Lewis acid catalysts suitable for use in the Friedel-Crafts reactions described herein are, for example, a metal, such as aluminum, cerium, copper, iron, molybdenum, tungsten or zinc; a Bronstead acid, such as a phosphoric acid, sulfuric acid, sulfonic acid, or a hydrohalo acid, such as hydrochloric or hydrobromic acid; halogen substituted acetic acids, such as chloroacetic or trifluoroacetic acids; or a metallic halide, such as a boron halide, zinc chloride, zinc bromide, berryl chloride, copper chloride, iron(III) bromide, iron(III) chloride, mercury(II) chloride, mercury(I) chloride, antimony bromide, antimony chloride, titanium(IV) bromide, titanium(IV) chloride, titanium(III) chloride, aluminum bromide or preferably aluminum chloride.

The compounds of Formula 1 wherein $X_1$ is at the ortho or para position and is a pyrrolidino, piperidino, morpholino, piperazino, N'-alkyl-piperazino and $NR_3R_4$ may be prepared as hereinabove described or may be prepared from a suitable fluorobenzoylimidazol-2-one of Formula 6

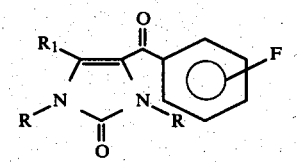

wherein R and $R_1$ are as defind above in Formula 1 and the fluorine atom is at either the ortho or para position. The appropriate compound of Formula 6 is allowed to react with from about 1 to about 10 molar equivalents of pyrrolidine, piperidine, morpholine, piperazine or N'-alkyl-piperazine, as appropriate. This reaction may be performed with or without a solvent, preferably, the amine is the solvent as well as the reactant. Suitable solvents, if desired, for this reaction are, for example, dimethylformamide; dimethylsulfoxide; petroleum ethers; chlorinated hydrocarbons, such as chloroform, methylene chloride, or carbon tetrachloride; carbon disulfide; ethereal solvents, such as diethyl ether, tetrahydrofuran or p-dioxan; aromatic solvents such as benzene, toluene or xylene; or alcoholic solvents, such as ethanol. The reaction is allowed to proceed for about ½ hour to about 48 hours, preferably about 24 hours, depending on the reactants, the solvent if any, and the temperature which can be from about 0° to about 150° C.

The compounds of Formula 1 wherein X is an amino group of the formula, —NR₃R₄, and wherein R₃ and R₄ are as defined in Formula 1, may alternatively be prepared from the corresponding nitro substituted benzoylimidazol-2-ones of Formula 7

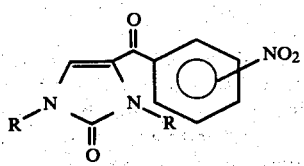

Formula 7 wherein R and R₁ are as defined in Formula 1. The compounds of Formula 7 are either known in the prior art or may be prepared by Friedel-Crafts acylation of an imidazol-2-one of Formula 4 with a nitro substituted benzoyl halide, preferably a nitro substituted benzoyl chloride by procedures analogous to those outlined above. The nitro group is reduced to the unsubstituted amino group by any suitable art-known procedure and subsequently, if desired, the unsubstituted amino may be alkylated by any appropriate art known method.

The nitrobenzoylimidazol-2-ones may suitably be converted to the corresponding aminobenzoylimidazol-2-ones by reduction with tin, zinc, iron or other suitable active metal in concentrated hydrochloric acid solution. About 1 molar equivalent to about 10 molar equivalents of the metal is used and the reaction is allowed to proceed for about ½ hour to about 10 hours, preferably about 2 or 3 hours depending upon the reactants and the temperature which can be from about 25° to about 150° C., preferably about 100° C. Alternatively, the nitrobenzoylimidazol-2-ones may be reduced catalytically with nickel, platinum, pallidium, or other similar suitable metals and molecular hydrogen. Such reactions are typically performed in an alcoholic solvent, preferably ethanol, but any nonreactive solvent may be used and the amount of metal catalyst may vary from about 0.001 molar equivalents to about 0.1 molar equivalents. The reaction is allowed to proceed for about 1 minute to about 1 hour, preferably about 10 minutes depending upon the reactants, the solvent and the temperature which can be from about 0° to about 100° C., preferably about 25° C. And alternatively, the nitrobenzoylimidazol-2-ones may be reduced with ammonium bisulfide (NH₄SH) in aqueous ammonia. About 1 to about 10 molar equivalents, preferably about 3 molar equivalents, of the bisulfide is allowed to react for about ½ hour to about 10 hours, preferably about 2 hours, depending upon the reactants and the temperature which may be from about 0° to about 150° C., preferably about 50° C. Finally, the nitrobenzoylimidazol-2-ones may be reduced to the corresponding amino compounds by any other appropriate art-known procedure.

The alkylation of the unsubstituted aminobenzoylimidazol-2-ones may be accomplished, for example, by reaction with one or more equivalents of an appropriate alkyl halide of the formulas R₃X and R₄X wherein R₃ and R₄ are as defined in Formula 1 and X is a halide. Typically these reactions are preformed in a solvent such as petroleum ethers; chlorinated hydrocarbons such as carbon tetrachloride, chloroform or methylene chloride; chlorinated aromatics such as 1,2,4-trichlorobenzene, o-dichlorobenzene or chlorobenzene; carbon disulfide; nitrobenzene; dimethylformamide; dimethylsulfoxide; ethereal solvents such as diethyl ether, tetrahydrofuran or p-dioxan; aromatic solvents such as benzene, toluene or xylene; alcohols such as methanol, ethanol or propanol; and aqueous alcohols such as aqueous ethanol. These alkylations are preferably performed in the presence of one or more equivalents of a "proton sponge" such as triethylamine, pyridine, sodium hydroxide, calcium hydroxide or potassium hydroxide to neutralize any hydrohalide as it is formed. Alternatively, the unsubstituted aminobenzoylimidazol-2-ones may be alkylated by any other appropriate art-known procedure such as reaction with formic acid and formaldehyde to form a dimethylamine compound. Furthermore, a variety of other substituents such as halogen and hydroxy may be prepared from the nitro substituted benzoylimidazol-2-ones of Formula 7 via the diazonium ion by procedures well known in the art.

The compounds of Formula 1 wherein X₁ or X₂ and X₃ are hydroxy may be prepared as hereinabove described or preferably may be prepared from a suitable alkoxy, preferably methoxy, substituted benzoylimidazol-2-one wherein the alkoxy group is at the position of desired hydroxy substitution. The alkoxy compound is cleaved to form the corresponding hydroxybenzoylimidazol-2-one by any suitable art-known procedure such as are taught by R. L. Burwell, "The Cleavage of Ethers," *Chem. Rev.* 54, 615–85 (1954) whose contents are hereby expressly incorporated by reference.

The X₁, X₂ and X₃ substituents may be protected as necessary in order to improve the stability of the Formula 5b and 5c reactants or to allow for the acylation of the imidazol-2-one ring nitrogen atoms as described herein without concurrent acylation of any reactive X groups. For example, where X₁, X₂ or X₃ is hydroxy, an amino group of the formula —NHR₃ or —SO₂NH₂, a benzyl group may be employed to block the otherwise reactive hydroxy or amino groups. The benzyl group may be removed subsequently by, for example, hydrogenolysis with hydrogen over a palladium catalyst or with sodium in liquid ammonia.

When desired, one or both of the nitrogen atoms of the imidazol-2-one ring may be substituted with an alkyl group by any art-known procedure. Such methods include reacting the appropriate N-unsubstituted aroylimidazol-2-one of this invention with a base and an alkylating agent in presence of an unreactive solvent. Suitable bases for this reaction can be, for example, a hydride such as sodium hydride or calcium hydride; a carbonate or bicarbonate such as sodium carbonate or sodium bicarbonate; a phenoxide such as sodium phenoxide; an alkoxide such as sodium ethoxide; or preferably a hydroxide such as sodium hydroxide. Suitable alkylating agents for this reaction are, for example, an alkyl halide such as methyl chloride, methyl bromide, or methyl iodide; or a dialkylsulfate such as dimethylsulfate. Suitable unreactive solvents are, for example, petroleum ethers; chlorinated hydrocarbons such as carbon tetrachloride, chloroform, or methylene chloride; chlorinated aromatics such as 1,2,4-trichlorobenzene, o-dichlorobenzene, or chlorobenzene; carbon disulfide; nitrobenzene; ethereal solvents such as diethyl ether, tetrahydrofuran or p-dioxan; aromatic solvents such as benzene, toluene or xylene; or preferably the polar aprotic solvents such as dimethylformamide (DMF) or dimethylsulfoxide (DMSO). The reaction is allowed to proceed from about 1 minute to about 1 hour and the temperature may be from about 0° to about 100° C., preferably about 25° C. When it is desired that only one of the imidazol-2-one nitrogen atoms be substituted with an alkyl group, the appropriate imidazol-2-one is reacted with from about 1 molar equivalent to about 10 molar equivalents of a base, preferably about 1 molar equivalent and with about 1 molar equivalent of an alkylating agent. Utilizing this procedure, both possible monoalkylated nitrogen isomers result. These isomers are separable by conventional art-known procedures such as fractional crystallization, fractional distillation, or chromatography. When it is desired that both nitrogen atoms of the imidazol-2-one ring by alkyl substituted, the appropriate imidazol-2-one is reacted with from about 2 molar equivalents to about 10 molar equivalents of a base, preferably about 2 molar equivalents and from about 2 molar equivalents to about 10 molar equivalents of an alkylating agent, preferably about 2 molar equivalents. Finally, any reactive substituents on the aroyl rings, if present, may become alkylated concurrently. That is, the following X groups, X=OH, —$NHR_3$, $SO_2NH_2$ and unsubstituted piperazino, are alkylated under identical reaction conditions. If desired, the alkylation of the aroyl ring substituents may be avoided by the use of suitable protecting groups well-known in the art, for example, X=OH or —$NHR_3$ may be benzylated and later deblcoked by hydrogenolysis.

When desired, the nitrogen atoms of the imidazol-2-one ring may be substituted with an alkylcarbonyl group by any suitable art-known procedure. Such methods include reacting the N-unsubstituted aroylimidazol-2-ones of this invention with an acyl halide, preferably an acyl chloride such as acetyl chloride, n-propanoyl chloride, isopropanoyl chloride or butanoyl chloride. Normally, acylation reactions utilizing acyl halides employ an acid sponge such as triethylamine or pyridine to remove any hydrohalide as it is formed. Furthermore, the corresponding free acid or acid anhydride may be employed instead of the acyl halides. Acylation reactions are generally run without added solvent but may be performed using any nonreactive solvent, for example, petroleum ethers; chlorinated hydrocarbons such as chloroform, methylene chloride or carbon tetrachloride; carbon disulfide; ethereal solvents, such as diethylether, tetrahydrofuran or p-dioxan or aromatic solvents such as benzene, toluene or xylene. The reactions are allowed to proceed for about 1 minute to about 100 hours, preferably from about 1 hour to about 10 hours and the temperature may be from about −78° to about 150° C., preferably from 0° to 100° C. Finally, any reactive substituents on the aroyl rings, if present, will become acylated concurrently. That is, the following X groups, X=OH, —$NHR_3$, —$SO_2NH_2$ and unsubstituted piperazino, are acylated under identical reaction conditions. If desired, the acylation of the benzoyl ring substituents may be avoided by the use of suitable protecting groups well-known in the art, for example X OH or —$NHR_3$ may be benzylated and later deblocked by hydrogenolysis.

The alkali metal, alkaline earth metal, transition metal, main group metal, ammonium or organic ammonium salts of the aroylimidazol-2-ones of this invention may be prepared from a corresponding metal or ammonium basic salt for example an alkoxide, such as sodium methoxide or sodium ethoxide; a phenoxide, such as sodium phenoxide; hydroxides, such as sodium hydroxide or potassium hydroxide; or a carbonate, such as sodium carbonate, potassium carbonate, zinc carbonate, magnesium carbonate or sodium hydrogen carbonate. These reactions may be performed with or without a solvent. Suitable solvents are, for example, lower alcohols, such as methanol, ethanol, isopropanol, n-propanol or n-butanol; aromatic solvents, such as benzene, toluene or xylene; ethereal solvents, such as diethyl ether, tetrahydrofuran or p-dioxan; and halogenated hydrocarbon solvents, such as chloroform, methylene chloride or carbon tetrachloride. The aroylimidazol-2-one and base are allowed to react for about 1 minute to about 24 hours depending on the reactants and the temperature which can be from about −78° to about 150° C., preferably from about 0° to about 25° C.

The aroyl chlorides or their corresponding carboxylic acids, which are required for the Friedel-Crafts acylation of this invention, are either generally available in the art or may be prepared by analogous procedures. The imidazol-2-one starting materials of Formula 4 may be prepared as described by or adapted from R. Duschinsky and L. A. Dolan, *J. Am. Chem. Soc.* 67, 2079 (1945), R. Duschinsky and L. A. Dolan, *J. Am. Chem. Soc.* 68, 2350 (1945) or U.S. Pat. No. 2,441,933.

The compounds of general Formula 1 may be used in the treatment of cardiac failure including congestive heart failure, backward heart failure, forward heart failure, left ventricular heart failure, or right ventricular heart failure or in the treatment of any other condition which requires the strenghtening of heart action with a cardiotonic. In many respects these compounds possess digitalis-like action. The compounds of general Formula 1 may also be used in the treatment of hypertension including primary or essential hypertension, hormonally induced hypertension, renal hypertension and chemically induced hypertension. The compounds of general Formula 1 may be used as antithrombotics, for example, in the treatment of arterial thrombosis. They affect the coagulation of blood by preventing the aggregation of blood platelets, which play a dominant role in thrombotic conditions both in the initial event and at the occlusive stage. Arterial thrombosis, particularly in arteries supplying the heart muscle and brain, is a leading cause of death and disability.

Formula I compounds have also been found to possess bronchodilator properties useful in the treatment of, for example, bronchial asthma. Bronchial asthma is typified by mild coughing, wheezing and shortness of breath. An attack may be brief in duration or prolonged over several days and is usually precipitated by exposure to various allergens or infection as well as a variety of other factors. Such attacks are characterized by narrowing of the airways due to bronchial spasm, edema and inflamation. Finally, formula 1 compounds have been found to possess uterospasmolytic properties useful in the treatment of, for example, premature labor. Premature labor, arbitrarily defined as labor prior to the 37th week of gestation will inevitably result in low birth weight infants substantially lacking, for example, essential lung and liver development. Premature birth is a major cause of infant mortality.

The compounds of this invention can be administered orally; parenterally, for example, subcutaneously, intravenously, intramuscularly or intraperitoneally; by depot injection; by implant preparation; when used as a bronchodilator by intranasal installation or by application to the mucous membranes, such as, that of the nose, throat and bronchial tubes, for example, in an aerosol spray containing small particles of a compound of this invention in a spray or dry powder form; and when used as a uterospasmolytic by rectal or vaginal suppositories.

The quantity of novel compound administered will vary depending on the patient, the mode of administration and severity of the condition to be treated and can be any effective amount. Repetitive daily administration of the compounds may be desired and will vary with the patient's condition and the mode of administration.

For oral administration, an effective amount of a formula 1 compound is from about 0.01 mg/kg (milligrams per kilograms) to about 500 mg/kg of patient body weight per day, preferably the antihypertensively effective amount is from 0.1 mg/kg to 25 mg/kg of patient body weight per day, the cardiotonically effective amount is from 0.1 mg/kg to 25 mg/kg of patient body weight per day, the antithrombotically effective amount is from 0.1 mg/kg to 25 mg/kg of patient body weight per day, and the bonchodilatory and uterospasmolytically effective amount is from 0.01 mg/kg to 500 mg/kg of patient body weight per day. More preferably, the bronchodilatory and uterospasmolytically effective amount is from 0.1 mg/kg to 25 mg/kg of patient body weight per day. For example, the desired effects can be obtained by consumption of a unit dosage form such as a tablet containing 1.0 to 200 mg of the active ingredient taken 1 to 4 times daily.

For parenteral administration, an effective amount of a formula 1 compound is from about 0.01 mg/kg to about 150 mg/kg of patient body weight per day. Preferably, the antihypertensively effective amount is from 0.1 mg/kg to 15 mg/kg of patient body weight per day, more preferably from 1.0 mg/kg to 10 mg/kg of patient body weight per day; the cardiotonically effective amount is from 0.1 mg/kg to 15 mg/kg of patient body weight per day; the antithrombotically effective amount is from 1 mg/kg to 25 mg/kg of patient body weight per day, and the bronchodilatory and uterospasmolytically effective amount is from 0.01 mg/kg to 150 mg/kg of patient body weight per day, more preferably from 0.1 mg/kg to 15 mg/kg of patient body weight per day. For example, the desired effects can be obtained by administration of a unit dosage form such as an intramuscular injection containing 1 to 50 mg of the active ingredient taken 1 to 4 times daily.

For aerosol administration the bronchodilatory effective amount of a formula 1 compound is from about 0.01 mg/kg to about 150 mg/kg of patient body weight per day, preferably from 0.1 mg/kg to 10 mg/kg of patient body weight per day. For example, the desired effects can be obtained by administration of a unit dosage form such as an aerosol spray of a 5 percent solution of the active ingredient taken 1 to 4 times daily.

For suppository administration, the uterospasmolytically effective amount of a formula 1 compound is from about 0.01 mg/kg to 150 mg/kg of patient body weight per day, preferably from 0.1 mg/kg to 20.0 mg/kg of patient body weight per day.

As used herein the term patient is taken to mean a warm blooded animal, for example, birds, such as chickens and turkeys, and mammals, such as primates, humans, sheep, horses, bovine cows and bulls, pigs, dogs, cats, rats and mice.

For oral administration the compounds can be formulated into solid or liquid preparations such as capsules, pills, tablets, troches, lozenges, melts, powders, solutions, suspensions or emulsions. The solid unit dosage forms can be a capsule which can be of the ordinary gelatin type containing, for example, surfactants, lubricants and inert filler, such as lactose, sucrose, and cornstarch. In another embodiment the compounds of general Formula 1 can be tableted with conventional tablet bases such as lactose, sucrose, and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

The compounds can be administered in the form of, for example, rectal or vaginal, suppositories in which a compound of formula 1 is incorporated into a base such as cocoa butter, glycerinated gelatin or polyethylene glycol polymers. Ideally, the base chosen will melt, more or less readily, at body temperatures, and will release the active ingredient in a form readily absorable via the appropriate mucosa. Suppository dosage forms can be prepared by, for example, cold compression or molding shapes from melted mixtures. Other common expients may be used to modify the properties in order to facilitate manufacture, storage or bioavailability.

The compounds can be administered as aerosols in solution or suspension and may be packaged in a pressurized aerosol container together with suitable propellants, for example, hydrocarbon propellants such as propane, butane or isobutane or carbon dioxide, nitrogen or other environmentally acceptable propellants with the usual adjuvants as may be necessary or desirable. The compounds also may be administered in a non-pressurized form such as in a nebulizer or atomizer. Preferably, the compound will be administered in a metered dose inhaler.

The following specific examples further illustrate the preparation and use of compounds employed in the instant invention.

EXAMPLE 1

1,3-Dihydro-4-(4-fluorobenzoyl)-5-methyl-2$\underline{H}$-imidazol-2-one

To a stirred mixture of 98.1 g (1 mole) of 1,3-dihydro-4-methyl-2$\underline{H}$-imidazol-2-one, 266.7 g (2 mole) of anhydrous aluminum chloride and 500 ml of nitrobenzene is added dropwise over 10 minutes, 158.6 g (1 mole) of p-fluorobenzoyl chloride. The mixture is stirred at 60°-65° C. for 6 hours, then poured on 2 kg of ice. The resulting precipitate is washed with diethyl ether and water and is recrystallized from 1.2 liters of dimethylformamide to give 131 g of the title compound. M.P. 289°-292° C.

EXAMPLE 2

1,3-Dihydro-4-methyl-5-[4-(1-piperidinyl)benzoyl]-2H-imidazol-2-one

A suspension of 11.0 g (0.05 mole) of 1,3-dihydro-4-(4-fluorobenzoyl)-5-methyl-2H-imidazol-2-one in 30 ml of piperidine is stirred at reflux temperature for 24 hours. Excess piperidine is evaporated under reduced pressure and the residue is recrystallized twice from a mixture of isopropanol and water to give 11.9 g of the title compound. M.P. 260°-263° C.

EXAMPLE 3

1,3-Dihydro-4-methyl-5-[4-(4-morpholinyl)benzoyl]-2H-imidazol-2-one

Following the procedure of Example 2 but substituting morpholine for piperidine, the title compound is obtained. M.P. 283°-286° C.

EXAMPLE 4

1,3-Dihydro-4-[4-(dimethylamino)benzoyl]-5-methyl-2H-imidazol-2-one

A mixture of 11.0 g (0.05 mole) of 1,3-dihydro-4-(4-fluorobenzoyl)-5-methyl-2H-imidazol-2-one, 100 ml of 30% aqueous solution of dimethylamine and 200 ml of ethanol is heated in a pressure bomb at 130°-135° C. for 22 hours. The mixture is cooled, the solid is collected and recrystallized from isopropanol-water to give the title compound. M.P. >310° C. λ(max)(methanol) 364 nm ($\epsilon$=23,300).

EXAMPLE 5

1,3-Dihydro-4-(4-hydroxybenzoyl)-5-methyl-2H-imidazol-2-one

To a melt of 26 g (0.23 mole) of pyridine hydrochloride at 200°-205° C. is added 5.3 g (0.023 mole) of 1,3-dihydro-4-(4-methoxybenzoyl)-5-methyl-2H-imidazol-2-one and the mixture is stirred mechanically for 30 minutes. The reaction mixture is poured on ice-2NHCl. The resulting precipitate is washed with water and recrystallized from isopropanol-water to give the title compound. M.P. >300° C. λ(max)(methanol) 320 nm ($\epsilon$=13,200).

EXAMPLE 6

1,3-Dihydro-4-methyl-5-[4-(methylthio)benzoyl]-2H-imidazol-2-one

A solution of 25.0 g of 4-(methylthio)-benzoic acid and 22 ml of thionyl chloride in 50 ml of benzene is refluxed for 4 hours. Excess reagent and solvent is evaporated and the residue is azeotroped 3 times with benzene to remove all thionyl chloride. The residue is added dropwise to a mixture of 11.8 g of 1,3-dihydro-4-methyl-2H-imidazol-2-one, 40.0 g of anhydrous aluminum chloride and 100 ml of nitrobenzene. The resulting mixture is stirred at 60°-65° C. for 5 hours, poured on ice and the precipitate that forms is collected, washed with ethyl ether and water, and recrystallized from isopropanol-water to give the title compound. M.P. 255°-258° C. (dec.).

EXAMPLE 7

1,3-Dihydro-4-(4-methoxybenzoyl)-5-methyl-2H-imidazol-2-one

To 19.6g of 1,3-dihydro-4-methyl-2H-imidazol-2-one and 53.2 g of anhydrous aluminum chloride in 150 ml of nitrobenzene is added dropwise 34.2 g of p-methoxybenzoyl chloride and the mixture is poured on 500 ml of 2N-HCl and ice, washed 3 times with ethyl ether, the resulting solid is recrystallized from isopropanol-water to give the title compound. M.P. 257°-258° C. (dec.).

EXAMPLE 8

1,3-Dihydro-4-(4-methoxybenzoyl)-5-methyl-2H-imidazol-2-one, sodium salt

To 7.0 g of 1,3-dihydro-4-(4-methoxybenzoyl)-5-methyl-2H-imidazol-2-one in 100 ml of methanol is added 1.6 g of sodium methoxide. The mixture is heated on a steam bath until homogeneous, filtered and evaporated to dryness. The solid residue is recrystallized from isopropanol to give the title compound. M.P. 280°-282° C. (dec.).

EXAMPLE 9

4-Benzoyl-1,3-dihydro-5-methylimidazol-2-one

To a solution of 3.0 g of 4-methylimidazol-2-one and 8.0 g of aluminum chloride in 50 ml of nitrobenzene is added dropwise 4.6 g of benzoyl chloride. The solution is warmed at 60° C. for 4 hours, poured over ice water, slurried with ether and the resulting solids filtered and dried to yield the title compound. M.P. 250°-54° C.

EXAMPLE 10

1,3-Dihydro-4-methyl-5-thienoyl-2H-imidazol-2-one

To a solution of 7.3 g of 4-methylimidazol-2-one and 10.8 g of aluminum chloride in 150 ml of nitrobenzene is added 12.0 g of 2-thienoyl chloride. The mixture is stirred at 60° C. for 3 hours, cooled and poured over ice water. The organic portion is extracted into ethyl acetate, dried and the organic solvent evaporated to give the title compound. M.P. 212°-215° C.

EXAMPLE 11

1,3-Dihydro-4-(3,4-dimethoxybenzoyl)-2H-imidazol-2-one

To a solution of 6.5 g of 1,3-dihydro-4-methyl-2H-imidazol-2-one and 14.6 g of aluminum chloride in 65 ml of nitrobenzene is added 17.6 g of 3,4-dimethoxybenzoyl chloride in portions. The mixture is stirred for 3 hours at 60° C., cooled and poured over ice water. The gummy solids are filtered and recrystallized twice from ethyl alcohol-water to afford the title compound. M.P. 257°-259° C.

EXAMPLE 12

1,3-Dihydro-4-(2-furanoyl)-5-methyl-2H-imidazol-2-one

To a slurry of 8.9 g of 1,3-dihydro-4-methyl-2H-imidazol-2-one and 24.0 g of aluminum chloride in 135 ml of nitrobenzene is added 12.9 g of furanoyl chloride in a dropwise manner. The mixture is stirred at 60° C. for 3 hours, cooled and poured over ice water. The solid is then filtered and recrystallized twice from methyl alcohol to afford the title compound. M.P. 214°-216° C.

EXAMPLE 13

1,3-Dihydro-4-(2-thienoyl)-2H-imidazol-2-one

In 50 ml of nitrobenzene is combined 13.3 g of aluminum chloride, 4.2 g of 1,3-dihydro-2H-imidazol-2-one and 8.1 g of thienoyl chloride. The mixture is stirred at 60° C. for 3 hours and poured over ice water. The solids are filtered, washed with ether and recrystallized twice from ethanol-water to afford the title compound. M.P. 339°–42° C.

EXAMPLE 14

4-Benzoyl-1,3-dihydro-2H-imidazol-2-one

To 51 ml of nitrobenzene is added 1.68 g of 1,3-dihydro-2H-imidazol-2-one, 5.3 g of aluminum chloride and 3.1 g of benzoyl chloride. The mixture is stirred for 3 hours at 60° C. and poured into ice water. The solids are filtered, washed with ether and recrystallized twice from methyl alcohol-water to afford the title compound. M.P. 329°–30° C.

EXAMPLE 15

1,3-Dihydro-4-furanoyl-2H-imidazol-2-one

To 50 ml of nitrobenzene is added 4.2 g of 1,3-dihydro-2H-imidazol-2-one, 13.3 g of aluminum chloride and 7.2 g of furanoyl chloride. The mixture is stirred at 60° C. for 3 hours and poured over ice water. The solids are filtered, washed with ether and recrystallized twice from ethanol-water to afford the title compounds. M.P. 318°–321° C.

EXAMPLE 16

1,3-Dihydro-4-(3,4-methylenedioxybenzoyl)-5-methyl-2H-imidazol-2-one

To 5.13 g. of 1,3-dihydro-4-methyl-2H-imidazol-2-one and 7.98 g. of anhydrous aluminum chloride in 80 ml. of nitrobenzene is added dropwise 10.60 g. of 3,4-methylenedioxybenzoyl chloride and the mixture is poured on 500 ml. of 2N-HCl and ice, washed 3 times with ethyl ether, the resulting solid is collected to give the title compound. M.p. 293°–296° C. (dec.).

EXAMPLE 17

1,3-Dihydro-4-(4-methoxybenzoyl)-1,3,5-trimethyl-2H-imidazol-2-one

In 120 ml of DMSO is placed 15.2 g of powdered potassium hydroxide, 8.0 g of 1,3-dihydro-4-(4-methoxybenzoyl)-5-methyl-2H-imidazol-2-one, sodium salt and 19.5 g of methyl iodide. The mixture is stirred at room temperature for 60 minutes and poured into 800 ml of water. Extraction with methylene chloride gives a solid, which is crystallized from ether. M.p. 109°–111° C. NMR: N—CH$_3$ (6 protons) at 3.3 ppm.

EXAMPLE 18

1,3-Dihydro-(1 or 3),5-dimethyl-4-(4-methoxybenzoyl)-2H-imidazol-2-one

To 2.0 g of 1,3-dihydro-4-(4-methoxybenzoyl)-5-methyl-2H-imidazol-2-one in 30 ml of DMSO is added 0.288 g of sodium hydride and 1.22 g of methyl iodide. The mixture is stirred at 22° C. for 30 minutes, poured into methylene chloride and washed with water. The solvent is dried and evaporated to give an oil which when triturated with chloroform gives a solid. The solid is crystallized from methanol; m.p. 225°–228° C.

Anal. calcd. for $C_{12}H_{14}N_2O_3$: C, 63.40; H, 5.73; N, 11.39; Found: C, 63.34; H, 5.85; N, 11.21;

NMR: N-Methyl; Singlet at 3.2 ppm.

EXAMPLE 19

1,3-Dihydro-4-ethyl-5-(4-methylsulfonylbenzoyl)-2H-imidazol-2-one

In 100 g polyphosphoric acid is placed 2.0 g p-(methylsulfonyl)benzoic acid and 1.12 g 1,3-dihydro-4-ethyl-2H-imidazol-2-one. The mixture is heated to 150° C. for 5 hours, cooled and quenched with 1000 ml of water. The title compound, which separates as a solid, is collected and washed with water.

By substituting 4-(methylsulfinyl)benzoic acid for 4-(methylsulfonyl)benzoic acid in the above procedure, the compound 1,3-dihydro-4-ethyl-5-(4-methylsulfinylbenzoyl)-2H-imidazol-2-one is obtained.

EXAMPLE 20

Use of 1,3-dihydro-4-(4-methoxybenzoyl)-5-methyl-2H-imidazol-2-one as an antihypertensive 100 mg/kg of the title compound is administered orally to six spontaneously hypertensive rats. This does results in a 40% decrease, on the average, in the blood pressure within 15 minutes of administration.

EXAMPLE 21

Use of 1,3-dihydro-4-(4-methoxybenzoyl)-5-methyl-2H-imidazol-2-one as a cardiotonic Heart failure is induced in a dog by administering sodium pentobarbitol (20 mg/kg) or propranalol hydrochloride (3 mg/kg) to the blood perfusing the heart. Following administration of either of these cardiac depressants the right atrial pressure increased dramatically and cardiac output is severely depressed. Administration of the title compound (1 mg/kg) reverses the failure as indicated by reversal of the right atrial pressure and cardiac output to near pretreatment levels.

EXAMPLE 22

Use of 1,3-dihydro-4-(4-methoxybenzoyl)-5-methyl-2H-imidazol-2-one as an antithrombotic When adenosine diphosphate is added to citrated platelet rich human plasma a typical aggregation of blood platelets occurs. However, if the title compound is added to the citrated platelet rich human plasma in concentrations of 3, 10, 30 and 100 µg/ml and subsequently adenosine diphosphate is added, the aggregation of blood platelets is inhibited 33, 49, 82 and 98%, respectively.

EXAMPLE 23

Preparation of a Tablet Formulation

|     |                                                              | Per Tablet |
| --- | ------------------------------------------------------------ | ---------- |
| (a) | 1,3-Dihydro-4-(4-methoxybenzoyl)-5-methyl-2H-imidazol-2-one  | 100 mg     |
| (b) | Cornstarch                                                   | 15 mg      |
| (c) | Lactose                                                      | 33.5 mg    |
| (d) | Magensium stearate                                           | 1.5 mg     |

EXAMPLE 24

Preparation of a Parenteral Formulation

| (a) | 1,3-Dihydro-4-(4-methoxybenzoyl)-5-methyl-2H-imidazol-2-one | 1.000 g |
|---|---|---|
| (b) | Polyoxyethylene sorbitan monooleate | 2.000 g |
| (c) | Sodium chloride | 0.128 g |
| (d) | Water for injection qs ad | 20.000 ml |

We claim:

1. A compound of the formula

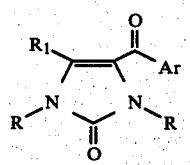

wherein Ar is 2-furyl, 2-thienyl, phenyl monosubstituted at the ortho, meta or para position with $X_1$, or disubstituted phenyl substituted at the para position with $X_2$ and at the ortho or meta position with $X_3$; $X_1$ is halogen, a straight or branched chain lower alkyl of from 1 to 4 carbon atoms, a straight or branched chain lower alkoxy of from 1 to 4 carbon atoms, a straight or branched chain lower alkylthio of from 1 to 4 carbon atoms, a straight or branched chain lower alkylsulfoxide of from 1 to 4 carbon atoms, a straight or branched chain lower alkylsulfone of from 1 to 4 carbon atoms, trifluoromethyl, $-SO_2N(R_2)_2$, $NR_3R_4$, pyrrolidino, piperidino, morpholino, piperazino or N'-alkyl-piperazino; $X_2$ and $X_3$ are halogen, a straight or branched chain lower alkoxy of from 1 to 4 carbon atoms, a straight or branched chain lower alkyl of from 2 to 4 carbon atoms, or when $X_3$ is at the meta position $X_2$ and $X_3$ together may be methylenedioxy optionally substituted by one or two methyl groups; R is hydrogen, a straight or branched chain lower alkyl of from 1 to 4 carbon atoms, a straight or branched chain lower alkylcarbonyl of from 1 to 4 carbon atoms, or a benzoyl; each of $R_1$, $R_2$, $R_3$ and $R_4$ are hydrogen or a straight or branched chain lower alkyl of from 1 to 4 carbon atoms with the proviso that both $R_3$ and $R_4$ cannot be hydrogen; or a pharmaceutically acceptable salt thereof.

2. A compound of claim 1 wherein R is hydrogen and $R_1$ is hydrogen or a straight or branched chain lower alkyl of from 1 to 4 carbon atoms.

3. A compound of claim 1 wherein R is hydrogen and $R_1$ is hydrogen, methyl or ethyl.

4. A compound of claim 3 wherein Ar is phenyl monosubstituted with $X_1$.

5. A compound of claim 4 wherein $X_1$ is a straight or branched chain lower alkylthio of from 1 to 4 carbon atoms, or a straight or branched chain lower alkylsulfoxide of from 1 to 4 carbon atoms or a straight or branched chain lower alkylsulfone of from 1 to 4 carbon atoms.

6. A compound of claim 5 wherein $X_1$ is at the para position.

7. A compound of claim 6 wherein $X_1$ is methylthio and $R_1$ is methyl.

8. A compound of claim 3 wherein Ar is disubstituted phenyl substituted at the para position with $X_2$ and at the ortho or meta position with $X_3$.

9. A compound of claim 8 wherein $X_3$ is at the meta position.

10. A compound of claim 9 wherein $X_2$ and $X_3$ are straight or branched chain lower alkoxy of from 1 to 4 carbon atoms or together may be methylenedioxy optionally substituted by one or two methyl groups.

11. A compound of claim 10 wherein $R_1$ is methyl and $X_2$ and $X_3$ are methoxy.

12. A compound of claim 11 wherein $R_1$ is methyl and $X_2$ and $X_3$ together are methylenedioxy.

13. A method for the treatment of cardiac failure in a patient in need thereof which comprises administering to said patient a cardiotonically effective amount of a compound of the formula

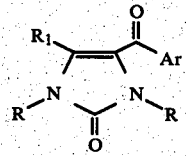

wherein Ar is 2-furyl, 2-thienyl, phenyl monosubstituted at the ortho, meta or para position with $X_1$, or disubstituted phenyl substituted at the para position with $X_2$ and at the ortho or meta position with $X_3$; $X_1$ is halogen, hydroxy, a straight or branched chain lower alkyl of from 1 to 4 carbon atoms, a straight or branched chain lower alkoxy of from 1 to 4 carbon atoms, a straight or branched chain lower alkylthio of from 1 to 4 carbon atoms, a straight or branched chain lower alkylsulfoxide of from 1 to 4 carbon atoms, or a straight or branched chain lower alkylsulfone of from 1 to 4 carbon atoms, trifluoromethyl, $-SO_2N(R_2)_2$, $NR_3R_4$, pyrrolidino, piperidino, morpholino, piperazino or N'-alkyl-piperazino; $X_2$ and $X_3$ are halogen, hydroxy, a straight or branched chain lower alkyl of from 1 to 4 carbon atoms, a straight or branched chain lower alkoxy of from 1 to 4 carbon atoms, or when $X_3$ is at the meta position, $X_2$ and $X_3$ together may be methylenedioxy optionally substituted by one or two methyl groups; R is hydrogen, a straight or branched chain lower alkyl of from 1 to 4 carbon atoms, a straight or branched chain lower alkylcarbonyl of from 1 to 4 carbon atoms, or a benzoyl; each of $R_1$, $R_2$, $R_3$ and $R_4$ are hydrogen or a straight or branched chain lower alkyl of from 1 to 4 carbon atoms; or a pharmaceutically acceptable salt thereof.

14. A method for the treatment of bronchial asthma in a patient in need thereof which conprises administering to said patient a bronchodilitory effective amount of a compound of the formula

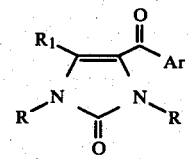

wherein Ar is 2-furyl, 2-thienyl, phenyl monosubstituted at the ortho, meta or para position with $X_1$, or disubstituted phenyl substituted at the para position with $X_2$ and at the ortho or meta position with $X_3$; $X_1$ is halogen, hydroxy, a straight or branched chain lower alkyl of from 1 to 4 carbon atoms, a straight or branched chain lower alkoxy of from 1 to 4 carbon atoms, a straight or branched chain lower alkylthio of from 1 to 4 carbon atoms, a straight or branched chain lower alkylsulfoxide of from 1 to 4 carbon atoms, or a straight or branched chain lower alkylsulfone of from 1 to 4 carbon atoms, trifluoromethyl, $-SO_2N(R_2)_2$, $NR_3R_4$, pyrrolidino, piperidino, morpholino, piperazino or N'-alkyl-piperazino; $X_2$ and $X_3$ are halogen, hydroxy, a straight or branched chain lower alkyl of from 1 to 4 carbon atoms, a straight or branched chain lower alkoxy of from 1 to 4 carbon atoms, or when $X_3$ is at the meta position, $X_2$ and $X_3$ together may be methylenedioxy optionally substituted by one or two methyl groups; R is hydrogen, a straight or branched chain lower alkyl of from 1 to 4 carbon atoms, a straight or branched chain lower alkylcarbonyl of from 1 to 4 carbon atoms, or a benzoyl; each of $R_1$, $R_2$, $R_3$ and $R_4$ are hydrogen or a straight or branched chain lower alkyl of from 1 to 4 carbon atoms; or a pharmaceutically acceptable salt thereof.

15. A method for the treatment of premature labor in a patient in need thereof which comprises administering to said patient a uterospasmolytically effective amount of a compound of the formula

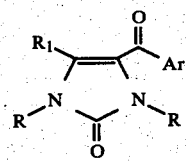

wherein Ar is 2-furyl, 2-thienyl, phenyl, phenyl monosubstituted at the ortho, meta or para position with $X_1$, or disubstituted phenyl substituted at the para position with $X_2$ and at the ortho or meta position with $X_3$; $X_1$ is halogen, hydroxy, a straight or branched chain lower alkyl of from 1 to 4 carbon atoms, a straight or branched chain lower alkoxy of from 1 to 4 carbon atoms, a straight or branched chain lower alkylthio of from 1 to 4 carbon atoms, a straight or branched chain lower alkylsulfoxide of from 1 to 4 carbon atoms, or a straight or branched chain lower alkylsulfone of from 1 to 4 carbon atoms, trifluoromethyl, $-SO_2N(R_2)_2$, $NR_3R_4$, pyrrolidino, piperidino, morpholino, piperazino or N'-alkyl-piperazino; $X_2$ and $X_3$ are halogen, hydroxy, a straight or branched chain lower alkyl of from 1 to 4 carbon atoms, a straight or branched chain lower alkoxy of from 1 to 4 carbon atoms, or when $X_3$ is at the meta position, $X_2$ and $X_3$ together may be methylenedioxy optionally substituted by one or two methyl groups; R is hydrogen, a straight or branched chain lower alkyl of from 1 to 4 carbon atoms, a straight or branched chain lower alkylcarbonyl of from 1 to 4 carbon atoms, or a benzoyl; each of $R_1$, $R_2$, $R_3$ and $R_4$ are hydrogen or a straight or branched chain lower alkyl of from 1 to 4 carbon atoms; or a pharmaceutically acceptable salt thereof.

16. A method of claim 13 wherein R is hydrogen, $R_1$ is a methyl group, and Ar is a 4-(methylthio)-phenyl group, that is the compound, 1,3-dihydro-4-methyl-5-[4-(methylthio)benzoyl]-2H-imidazol-2-one or a pharmaceutically acceptable salt thereof.

* * * * *

UNITED STATES PATENT AND TRADEMARK OFFICE
CERTIFICATE OF CORRECTION

PATENT NO. : 4,405,635
DATED : September 20, 1983
INVENTOR(S) : Richard A. Schnettler, et al.

It is certified that error appears in the above-identified patent and that said Letters Patent are hereby corrected as shown below:

At column 1, line 17, the patent reads "antihypertensive" and should read -- antihypertensives--.

At column 7, lines 8-15, the patent reads

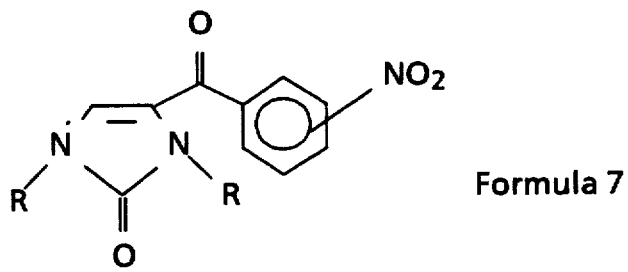

Formula 7 and should read

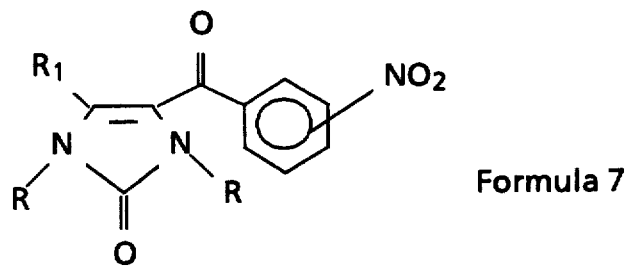

Formula 7

UNITED STATES PATENT AND TRADEMARK OFFICE
CERTIFICATE OF CORRECTION

PATENT NO. : 4,405,635

DATED : September 20, 1983

INVENTOR(S) : Richard A. Schnettler, et al.

It is certified that error appears in the above-identified patent and that said Letters Patent are hereby corrected as shown below:

At column 7, line 64, the patent reads "preformed" and should read --performed--.

At column 16, lines 25 and 26, the patent reads "This does results" and should read --This results--.

At column 18, line 50, the patent reads "conprises" and should read --comprises--.

Signed and Sealed this

Fifth Day of April, 1988

*Attest:*

DONALD J. QUIGG

*Attesting Officer*  *Commissioner of Patents and Trademarks*